(12) United States Patent
Nikonov et al.

(10) Patent No.: US 9,287,576 B2
(45) Date of Patent: Mar. 15, 2016

(54) SELF-POWERED INTERNAL MEDICAL DEVICE

(71) Applicants: Dmitri E. Nikonov, Morgan Hill, CA (US); Michael C. Mayberry, Beaverton, CA (US); Ian A. Young, Portland, OR (US); Kelin J. Kuhn, Aloha, OR (US)

(72) Inventors: Dmitri E. Nikonov, Morgan Hill, CA (US); Michael C. Mayberry, Beaverton, CA (US); Ian A. Young, Portland, OR (US); Kelin J. Kuhn, Aloha, OR (US)

(73) Assignee: Intel Corporation, Santa Clara, CA (US)

( * ) Notice: Subject to any disclaimer, the term of this patent is extended or adjusted under 35 U.S.C. 154(b) by 191 days.

(21) Appl. No.: 13/971,306

(22) Filed: Aug. 20, 2013

(65) Prior Publication Data

US 2015/0054468 A1 Feb. 26, 2015

(51) Int. Cl.
    *H01M 8/00* (2006.01)
    *H01M 8/16* (2006.01)
    *A61B 5/145* (2006.01)

(52) U.S. Cl.
    CPC ............. *H01M 8/16* (2013.01); *A61B 5/14503* (2013.01); *A61B 2560/0214* (2013.01); *H01M 2250/402* (2013.01)

(58) Field of Classification Search
None
See application file for complete search history.

(56) References Cited

U.S. PATENT DOCUMENTS

| | | | |
|---|---|---|---|
| 3,861,397 A * | 1/1975 | Rao et al. ...................... 607/35 |
| 3,941,135 A * | 3/1976 | von Sturm et al. ............. 607/35 |
| 5,771,471 A | 6/1998 | Alberth, Jr. et al. |
| 6,294,281 B1 * | 9/2001 | Heller ........................... 429/401 |
| 7,236,821 B2 * | 6/2007 | Cates et al. ...................... 607/2 |
| 7,485,212 B2 * | 2/2009 | Willner et al. ............. 204/403.14 |
| 7,709,134 B2 * | 5/2010 | Minteer et al. ................ 429/401 |
| 7,951,357 B2 * | 5/2011 | Gross et al. ..................... 424/9.6 |
| 8,380,310 B2 * | 2/2013 | Visco et al. ....................... 607/35 |
| 8,451,070 B2 | 5/2013 | Frazier et al. |
| 8,906,818 B2 | 12/2014 | Randall et al. |
| 2004/0158294 A1 | 8/2004 | Thompson |
| 2007/0296376 A1 | 12/2007 | Marquet et al. |
| 2008/0160384 A1 * | 7/2008 | Iqbal et al. ....................... 429/34 |
| 2009/0152867 A1 | 6/2009 | Cripps |
| 2009/0155644 A1 | 6/2009 | Cui et al. |
| 2009/0200983 A1 | 8/2009 | Dyer et al. |
| 2011/0250510 A1 * | 10/2011 | Cinquin et al. ............... 429/401 |

(Continued)

OTHER PUBLICATIONS

Barton et al., "Enzymatic Biofuel Cells for Implantable and Microscale Devices," 2004 Chem. Rev. 104, pp. 4867-4886.*

(Continued)

*Primary Examiner* — Leigh Garbowski
(74) *Attorney, Agent, or Firm* — Grossman, Tucker, Perreault & Pfleger, PLLC (57) ABSTRACT

This disclosure is directed to a self-powered internal medical device. An example device may comprise at least an energy generation module and an operations module to at least control the energy generation module. The energy generation module may include a structure to capture certain molecules in the organic body based at least on size, the structure including a surface of the device in which at least one opening is formed. The at least one opening may be sized to only capture certain molecules. The operations module may initiate oxidation reactions in the captured molecules to generate current for device operation or for storage in an energy storage module. Thermoelectric generation circuitry in the energy generation module may also use heat from the reaction to generate a second current. The operations module may control operation of a sensor module and/or communication module in the device based on the generated energy.

24 Claims, 7 Drawing Sheets

(56) References Cited

U.S. PATENT DOCUMENTS

2011/0264062 A1 10/2011 Locke et al.
2012/0171599 A1* 7/2012 Kishida et al. ............ 429/482

OTHER PUBLICATIONS

Kakehi et al., "A novel wireless glucose sensor employing direct electron transfer principle based enzyme fuel cell", Biosensors and Bioelectronics 22 (2007) 2250-2255, 2006 Elsevier, pp. 2250-2255.
Fabricating MEMX and Nanotechnology, downloaded from http://www.memsnet.org/mems/fabrication.html, 16 pages.
Hussian, "Ultimate low-power devices", Micro/Nano Lithography, downloaded from http://spie.org/x40697.xml? pf=true&ArticleID=x40697, 5 pages.
Rapoport, et al., "A Glucose Fuel Cell for Implantable Brain Machine Interfaces", PLoS One, vol. 7, Issue 6, Jun. 2012, downloaded from http://www.plosone.org/article/info%3Adoi%2F10.1371%2Fjournal.pone.0038436.
Taiwan Office Action from related case 103127763 mailed Jul. 31, 2015, including English translation.

* cited by examiner

SELF-POWERED INTERNAL MEDICAL DEVICE

TECHNICAL FIELD

The present disclosure relates to medical equipment, and more particularly, to a device implantable in an organic body that may generate power for operation based on the organic body.

BACKGROUND

An area where technological advancement is proceeding rapidly is in the equipment used for medical diagnosis and treatment. The achievements in this area have yielded tools that allow treating physicians, scientists, researchers, etc. to be more aware of various factors that may be indicative of illness in organic bodies (e.g., human beings, animals, etc.). Traditionally medical equipment was designed to work using an outside-in approach. This was necessary because the scale of the technology involved in medical diagnosis and treatment equipment was considerably larger than the space available inside the organic body being treated. However, developments in electronics have allowed medical devices to shrink substantially. Large-scale implanted devices such as pacemakers and heart-assist pumps may help to maintain a normal heartbeat. Examples of smaller devices may include pill-like cameras. These devices may be implanted or swallowed to record, and even wirelessly transmit, data regarding various operations inside an organic body.

However, as medical diagnostic and treatment devices shrink even smaller (e.g., to scales so small that devices may exist freely within the bloodstream of an organic body), problems are often encountered. Devices on the scale of microelectromechanical systems (MEMS) may have great potential in that certain monitoring or treatment operations may be performed continuously from within an organic body without the procedure being overly invasive or an impediment to a subject. However, implementing even rudimentary monitoring and transmission functionality on devices with so little real estate is problematic at best. Existing battery technologies have limited applicability in this area. For example, current lithium ion battery technology would render any such device too large to navigate the bloodstream safely, and charged capacitor batteries, while substantially smaller, cannot hold enough charge to be viable as a long term energy source.

BRIEF DESCRIPTION OF THE DRAWINGS

Features and Advantages of Various Embodiments of the Claimed Subject Matter Will Become Apparent as the Following Detailed Description Proceeds, and Upon Reference to the Drawings, Wherein Like Numerals Designate Like Parts, and in which:

Although the following Detailed Description will proceed with reference being made to illustrative embodiments, many alternatives, modifications and variations thereof will be apparent to those skilled in the art.

DETAILED DESCRIPTION

This disclosure is directed to a self-powered internal medical device. An example device may comprise at least an energy generation module and an operations module to at least control the energy generation module. The energy generation module may generate energy based on an organic body in which the device is implanted, and for this purpose may comprise a structure to capture certain molecules in the organic body based at least on size. An example structure may include a surface of the device in which at least one opening is formed. The at least one opening may be sized to capture certain molecules (e.g., low-density lipoprotein (LDL) molecules) and to allow other molecules to escape (e.g., smaller high-density lipoprotein (HDL) molecules). The operations module may initiate oxidation reactions in the captured molecules to generate current and heat. The current may be used to supply power to the operations module or for charging at least one energy storage module in the device. In addition, thermoelectric generation circuitry in the energy generation module may use the heat generated by the oxidation reaction to generate a second current for operations or energy storage. The operations module may control operation of a sensor module and/or communication module in the device based on the generated energy.

In one embodiment there is provided a device comprising, for example, at least an energy generation module and an operations module. The energy generation module may be to generate energy based on molecules captured from an organic body in which the device is implanted. For example, the molecules being captured based at least on size. The operations module may be to at least control operation of the energy generation module.

The energy generation module may be to cause a chemical reaction to occur in the captured molecules to at least generate electrical current. For example, the energy generation module may comprise at least one surface of the device in which is formed at least one opening, the at least one opening being sized to capture molecules of a first size and to allow molecules of a second size to escape capture. In one embodiment, the at least one surface may be formed on the device using silicon underetch with electrodes on the at least one surface and an opposing surface of the device, the electrodes being at least structurally coupled by a silicon via formed through the device. The molecules of a first size may be low-density lipoprotein (LDL) molecules and the molecules of a second size are high-density lipoprotein (HDL) molecules. The operations module may be to initiate an oxidation reaction in the captured LDL molecules by causing a voltage to be placed across the captured LDL molecules, the oxidation reaction causing a first electrical current and heat to be generated. In one embodiment, the energy generation module may comprise thermoelectric generation circuitry to generate a second electrical current based on the generated heat. At least one of the first electrical current or the second electrical current may be stored by at least one energy storage module also in the device. In one embodiment, the operations module may comprise at least a control module, a communication module and a sensor module. The control module may be to control the operation of the energy generation module by periodically supplying a voltage to the energy generation module. The sensor module may be to sense at least one characteristic of the organic body and the communication module is to transmit information about at least one of the device or the at least one characteristic via wireless communication. The control module may be further to control operation of at least one of the sensor module and the communication module based on the energy in the device. An example method consistent with at least one embodiment of the present disclosure may include capturing molecules from an organic body in which a device is implanted, the molecules being captured based at least on size, triggering energy generation in the device, the energy being generated based on the captured molecules, and controlling operations in the device based on the energy generation.

Figure 1:
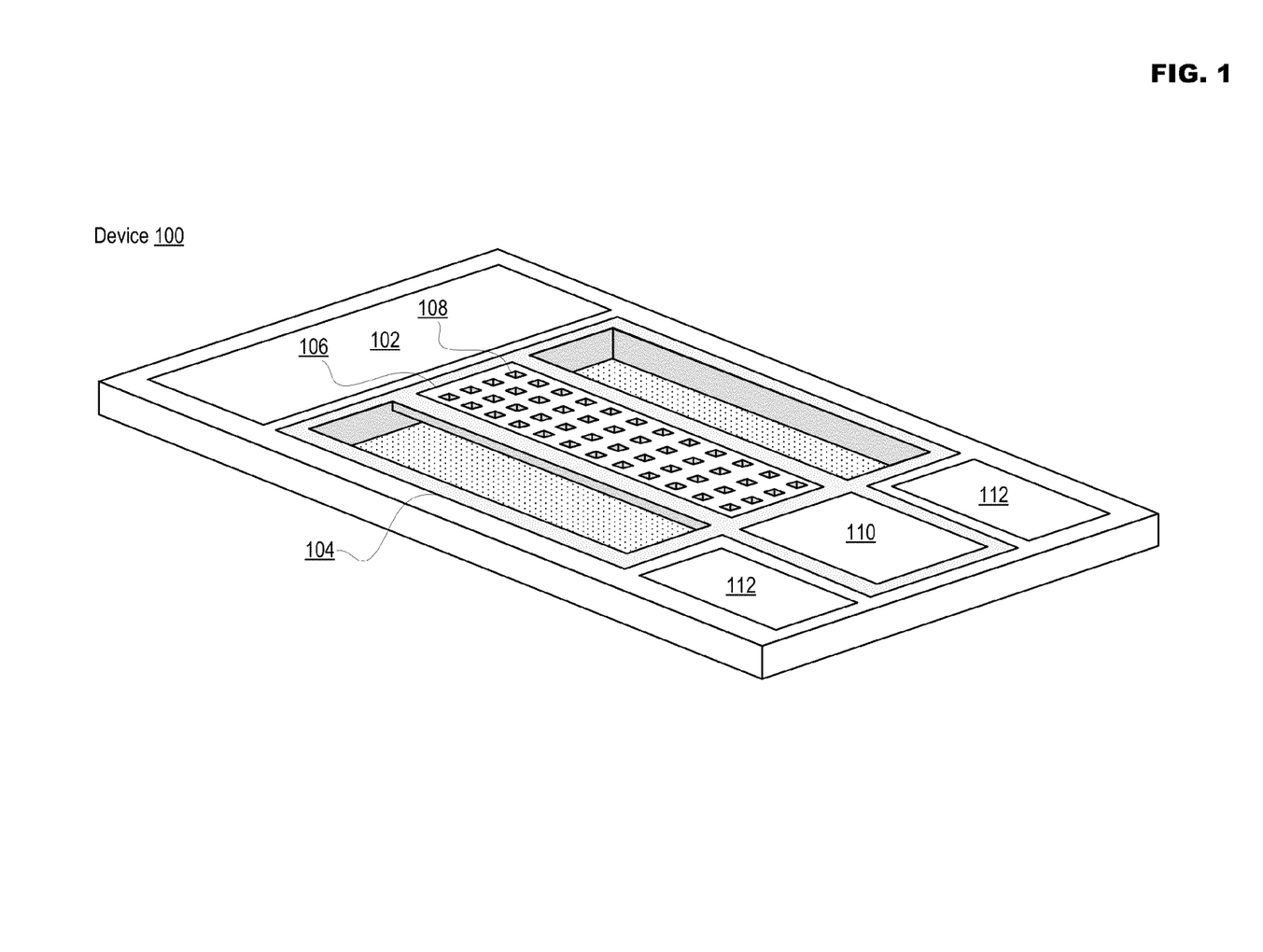
FIG. 1 illustrates an example self-powered internal medical device in accordance with at least one embodiment of the present disclosure.

FIG. 1 illustrates an example self-powered internal medical device in accordance with at least one embodiment of the present disclosure. Device 100 may be constructed from a single substrate (e.g., as a single integrated circuit or chip) or may be composed of multiple substrates bonded together to form a multichip module (MCM). One example application of device 100 is for monitoring a characteristic of an organic body (e.g., a human body, animal body, etc.). For example, device 100 may be inserted into the bloodstream of an organic body to monitor blood component levels such as, but not limited to, oxygenation, glucose, red and/or white cell counts, salt concentration, metabolism byproducts (e.g., acids, adenosine triphosphate (ATP), adenosine diphosphate (ADP), glycerol, etc.), for the existence of conditional precursors or markers (e.g., proteins including infection antibodies, toxins, cancer indicators, etc.), etc. Device 100 may also be inserted subcutaneously (e.g., under the skin, into a vessel or organ, etc.) of an organic body to monitor, for example, neuron electrical characteristics, concentration of neurotransmitters in synapses, stress from muscle contractions, exposure to sun, radiation, chemicals, etc. For use in an organic body, such as described above, device 100 may be implemented entirely on a single microscopic microchip. An example implementation may include dimensions of less than one millimeter in length, less than one millimeter in width and less than 0.1 millimeters in thickness.

Device 100 may comprise one or more modules for supporting device functionality. It is important to note that the quantity or orientation of these modules in the example shown in FIG. 1 is merely for the sake of explanation herein. The quantity or orientation of modules in device 100 may vary depending on, for example, an application for which device 100 is being designed. For example, device 100 may include operations module 102, energy generation module 104 and at least one energy storage module 112. Operations module 102 may control both device-centric operations (e.g., energy generation, management, etc.) and application-centric operations (e.g., body characteristic monitoring, device/characteristic-related communications, etc.). An example of a more-specific configuration for operations module 102 will be disclosed in regard to FIG. 4.

Energy generation module 104 may comprise at least one molecular sieve 106. At least one opening 108 may be formed in the surface of molecular sieve 106 to, for example, capture molecules from an organic body in which device 100 may be implanted. In the example of FIG. 1, molecular sieve 106 includes a plurality of openings 108. For example, device 100 may be formed on a substrate including a plurality of material layers. In one embodiment, openings 108 are intended to capture certain molecules (e.g., LDL molecules) existing in the organic body for use in generating a current for operating device 100. For example, operations module 102 may be configured to initiate a reaction (e.g., an oxidation reaction) in the captured molecules that results in electric current generation. The oxidation reaction may further generate heat as a byproduct, and in one embodiment energy generation module 104 may include thermoelectric generation module 110 for generating a second current based on the byproduct generated heat. While energy generation module 104 has been illustrated as comprising features for generating electrical current directly from molecular reactions and also from byproducts of the molecular reactions (e.g., heat), it is important to note that, consistent with the present disclosure, device 100 may include any current generation feature individually or all of these generation features.

In the example of FIG. 1 there are two energy storage modules 112 comprising battery structures such as capacitor arrays, etc. designed to hold energy. Energy storage modules 112 may be charged by a current resulting directly from the oxidation reaction. Further, a second current generated from the byproduct heat may also be used to charge energy storage modules 112. The energy stored in energy storage modules 112 may be provided to operations module 102 to provide energy for initiating oxidation reactions in captured molecules, for monitoring body characteristics, for communicating device information and/or body characteristics, etc.

Figure 2:
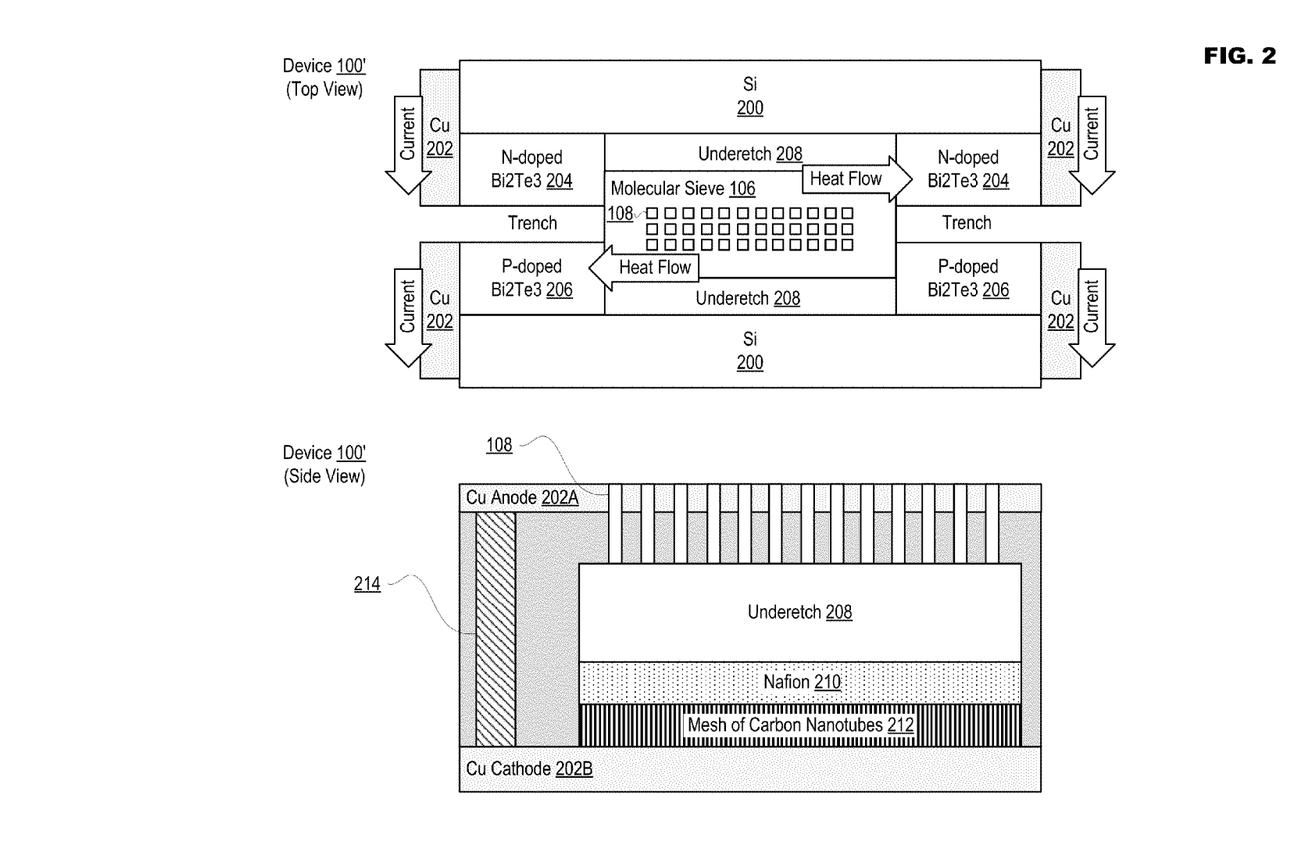
FIG. 2 illustrates example device construction in accordance with at least one embodiment of the present disclosure.

FIG. 2 illustrates example device construction in accordance with at least one embodiment of the present disclosure. It is important to note that the materials and/or structures described in FIG. 2 are merely examples provided for the sake of explanation, and are not intended to limit the construction of devices consistent with embodiments of the present disclosure to a particular composition. FIG. 2 includes a top view and a side view of example device 100'. As shown in the top view, various semiconductor fabrication processes may be employed to deposit materials on, or remove material from, silicon (Si) substrate 200. For example, Copper (Cu) 202 may be applied to Si 200 to conduct electrical current generated by Ni-doped bismuth telluride (Bi2Te3) 204 and P-doped Bi2Te3 206, also applied to Si 200, based on heat generated by molecular sieve 106 during molecular reactions. The at least one opening 108 may be formed in at least one of the layers using a semiconductor underetching material removal process as shown at 208. This allows molecules that are not to be captured to flow through openings 108 unimpeded and away from device 100' via underetch openings 208.

In the side view of device 100', Cu anode 202A and Cu cathode 202B may be applied to opposing surfaces (e.g. top and bottom) of device 100' (e.g., via a material deposition process) to catalyze reactions (e.g., the oxidation of lipoproteins), and may be at least structurally coupled by through silicon via 214. Device 100' may further comprise material layers to provide separation for the oxidation and reduction portions of reactions. For example, Nafion layer 210 may act as a charge selective membrane. Nafion 210 only allows conduction of H+ ions (protons), but not e− electrons. A mesh of carbon nanotubes 212 under Nafion 210 layer may provide both a good conductor and may catalyze the reduction of hydrogen into water.

Figure 3:
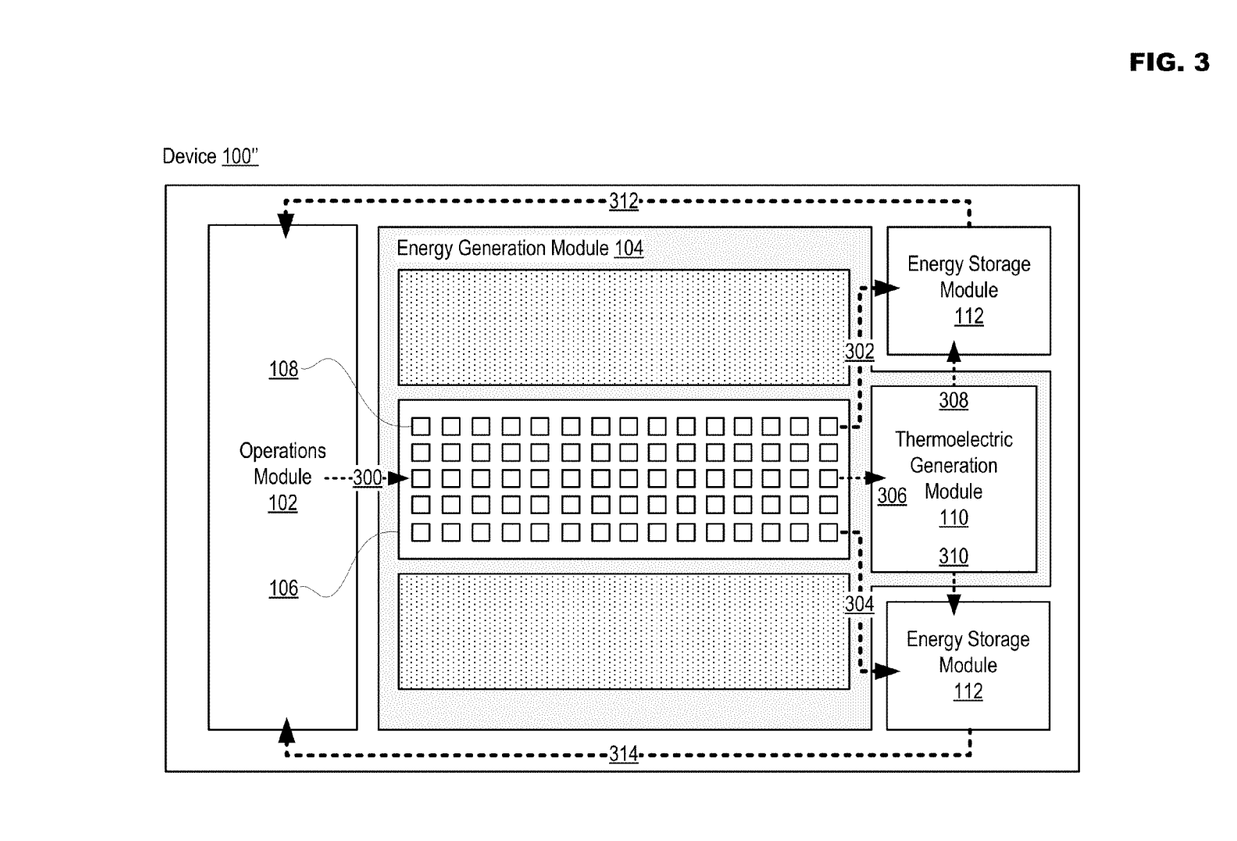
FIG. 3 illustrates an example configuration for a self-powered internal medical device in accordance with at least one embodiment of the present disclosure.

FIG. 3 illustrates example energy generation for a self-powered internal medical device in accordance with at least one embodiment of the present disclosure. Initially, molecular sieve 106 may capture certain molecules in device 100''. Operations module 102 may then initiate a reaction (e.g., may trigger an oxidation reaction) in the captured molecules as illustrated at 300. For example, initiating the reaction may comprise operations module 102 being configured to cause a voltage being to be placed across any captured molecules, the voltage being sufficient enough to initiate an oxidation reaction. Operations module 102 may cause the voltage to be placed across the captured modules periodically (e.g., based on an interval timer in device 100''), in response to sensing at least one molecule captured by molecular sieves 106, etc. Additional detail with respect to molecular capture and oxidation reaction will be disclosed in FIGS. 5 to 6.

Currents 302 and 304 generated by the oxidation reaction initiated at 300 may be used to charge energy storage modules 112. For example, energy generation module 104 may comprise circuitry to coupling molecular sieve 106 (e.g., and openings 108) to energy storage module 112. In one embodiment, heat 306 may be generated as a byproduct of the oxidation reaction. While not shown in FIG. 3, energy generation module 104 may also include a heat collection structure such as a heat sink to collect the heat generated from various oxidation reactions that may occur in molecular sieves 106. The heat collection structure may further be coupled to thermoelectric generation module 110, which may contain circuitry to convert the collected heat into a current or currents (e.g., currents 308 and 310) for charging energy storage module 112. Energy storage module 112 may then provide energy (e.g., currents 312 and 314) for use by operations module 102. While different line thicknesses have been employed at 300, 302, 304, 308, 310, 312 and 314 in FIG. 3 to represent examples of relative magnitude between energy that may be involved during different stages of energy generation in device 100', these relative magnitudes are merely for the sake of explanation in FIG. 3 and do not signify any particular values. Magnitudes such as shown in FIG. 3 may vary in different implementations consistent with the present disclosure.

Figure 4:
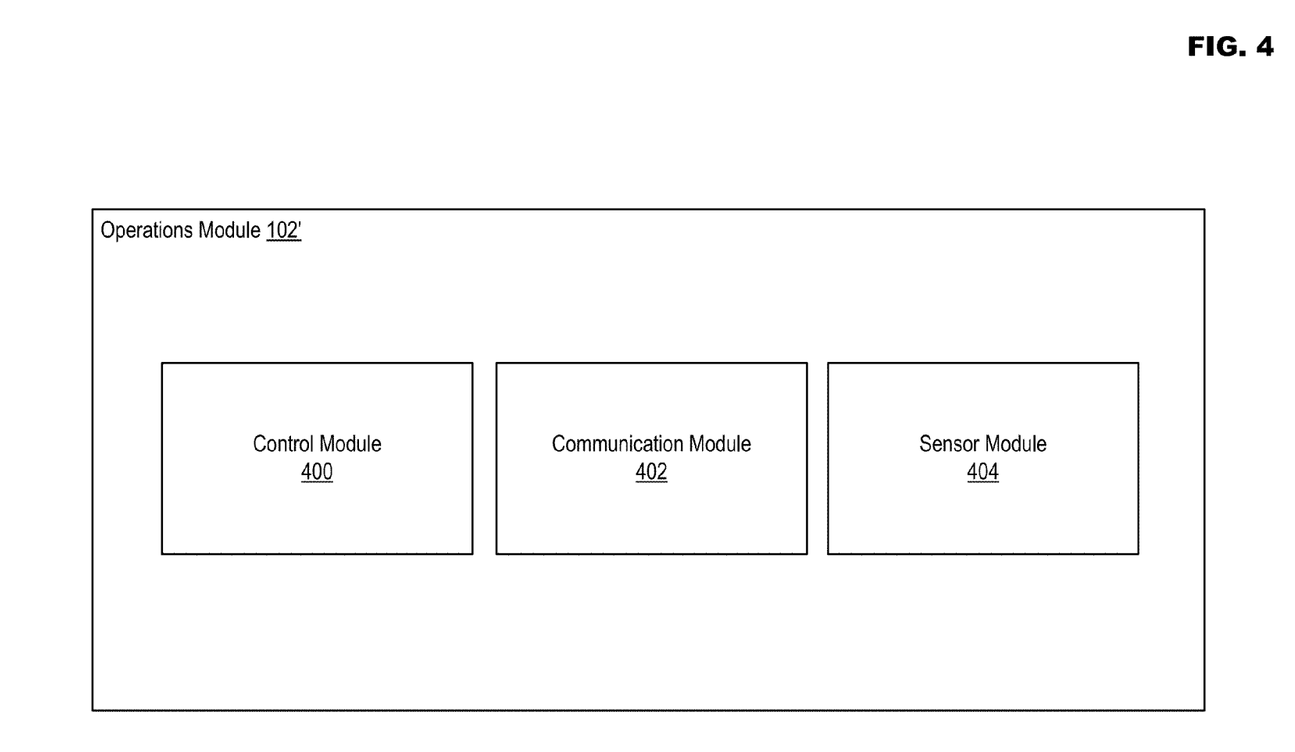
FIG. 4 illustrates example energy generation for an operations module in a self-powered internal medical device in accordance with at least one embodiment of the present disclosure.

FIG. 4 illustrates an example configuration for an operations module in a self-powered internal medical device in accordance with at least one embodiment of the present disclosure. Operations module 102' may include, for example, control module 400, communication module 402, and sensor module 404. Control module 400 may initiate oxidation reactions in captured molecules, may manage power in device 100, etc. For example, control module 400 may include at least a timer and corresponding circuitry configured to supply a voltage for initiating oxidation reactions on a periodic basis. Control module may also comprise circuitry configured to prevent operations in communication module 402 and/or sensor module 404 whenever the energy stored in energy storage modules 112 drops below a certain level. This may help to ensure that device 100 continues to have enough power to initiate oxidation reactions, and thus generate power. In a more complex implementation, operations module 102' may include some intelligence (e.g., a processor or microcontroller) capable of executing instructions stored in a memory (e.g., ROM, EPROM, Flash, etc.) also in operations module 102', the stored instructions causing control module to carry out some or all of the above power generation and/or management activities.

Communication module 402 may be to transmit device-related and body characteristic-related to monitoring equipment via wireless communication. For example, communication module 402 may be configured to communicate via close-proximity wireless communication, such as by responding to radio-frequency (RF) communication scan, or via short-range wireless communication such as Bluetooth, wireless local area networking (WLAN), etc. In the instance of RF communication, communication module 402 may receive power from an RF scanner that is located outside of the organic body. Signals emitted by communication module 402 may also be utilized to determine the location of device 100 within an organic body (e.g., by triangulation using receipt delay measured at different receivers external to the organic body). Device-related information may include device identification (ID) information, device condition information (e.g., current power level, operational alerts, etc.), device age/up-time, etc. Body characteristic information may include information collected by sensor module 404 about the organic body in which device 100 is implanted. Sensor module 404 may comprise sensors and corresponding circuitry to determine body characteristic information such as, for example, blood chemistry, tissue composition, the presence of conditional precursors (e.g., cancer indicators), etc. Sensor module 404 may then provide the determined body characteristic information to communication module 402 for transmission to an outside (e.g., outside the organic body) monitoring device.

Figure 5:
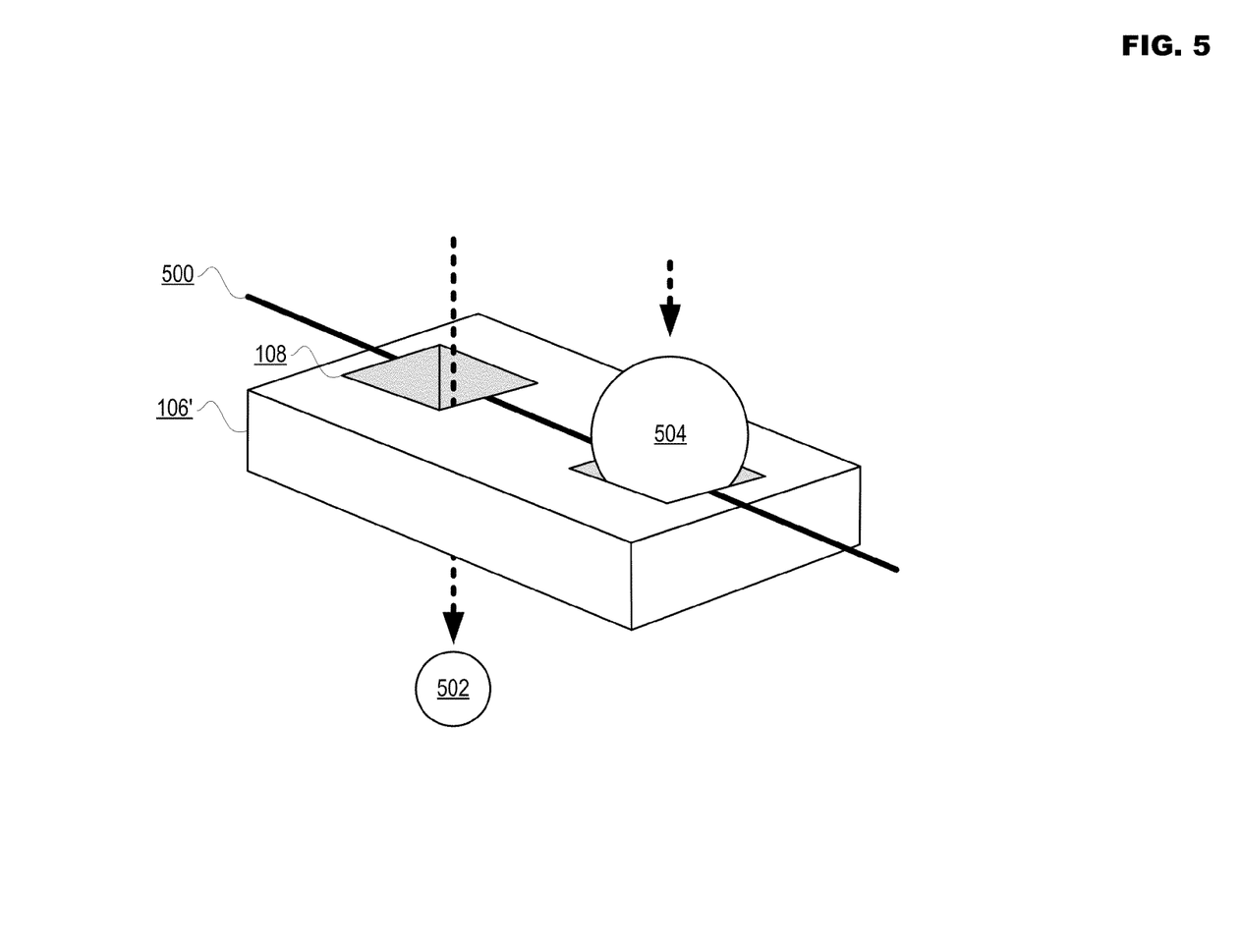
FIG. 5 illustrates an example of molecular capture in a self-powered internal medical device in accordance with at least one embodiment of the present disclosure.

FIG. 5 illustrates an example of molecular capture in a self-powered internal medical device in accordance with at least one embodiment of the present disclosure. A section of molecular sieve 106' is disclosed in FIG. 5. Circuitry 500 may be configured to supply a voltage for initiating an oxidation reaction in captured molecules. The capture of certain molecules may be predicated on the size of opening 108. For example, it may be desirable to only capture LDL molecules 504 while allowing HDL molecules 502 to escape capture. LDL molecules 504 may have average diameters in the range from approximately 18 nm to 28 nm, while HDL molecules 502 may have diameters in the range from approximately 5 nm to 15 nm. As illustrated in FIG. 5, selecting an opening size of, for example, approximately 18 nm may be large enough to allow HDL molecules 502 to escape but small enough to allow LDL molecules 504 to be captured.

Figure 6:
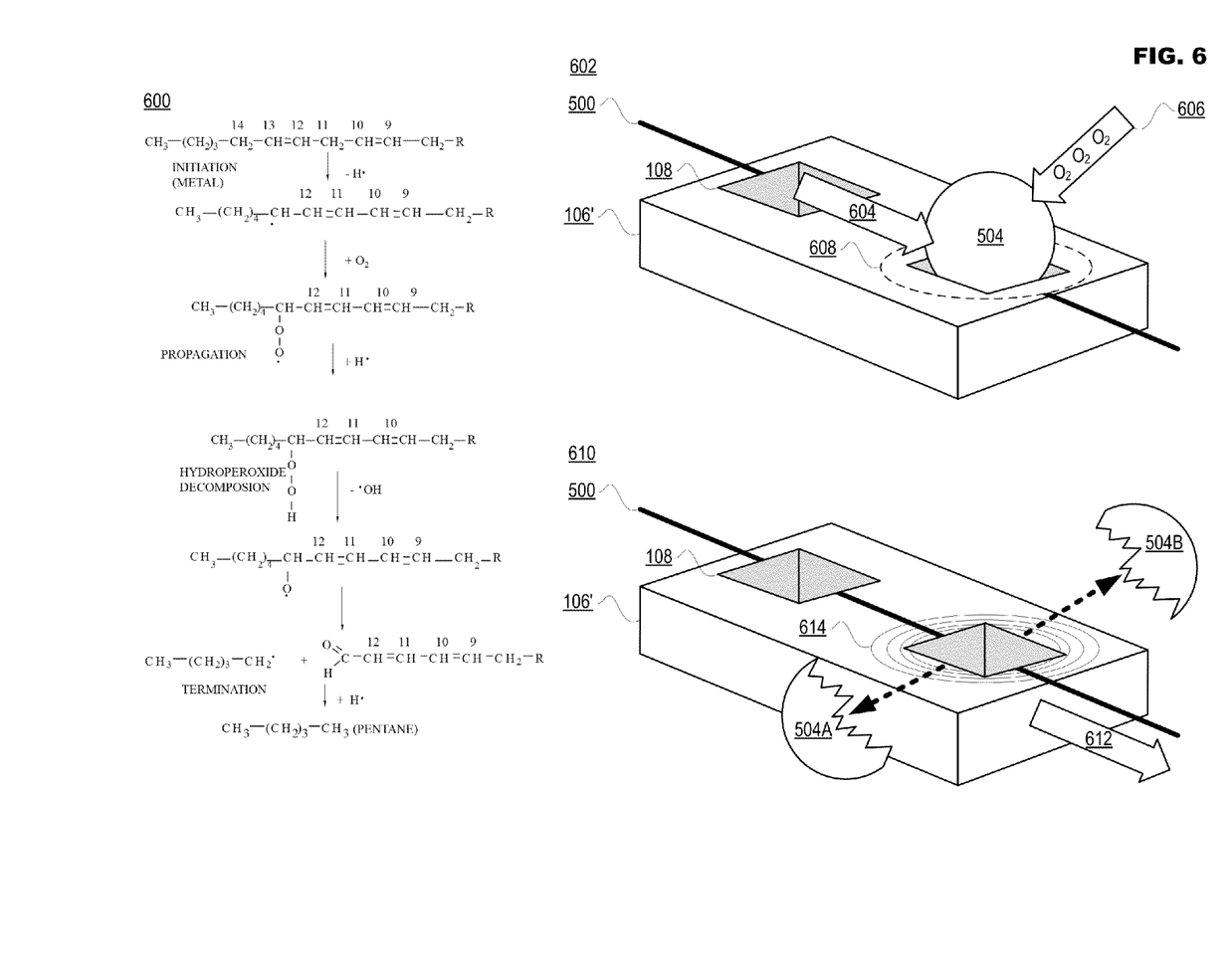
FIG. 6 illustrates an example of molecular oxidation in a self-powered internal medical device in accordance with at least one embodiment of the present disclosure.

FIG. 6 illustrates an example of molecular oxidation in a self-powered internal medical device in accordance with at least one embodiment of the present disclosure. Oxidation is the interaction between oxygen and other substances. During oxidation electrons may be lost from the substance being oxidized, and these electrons may be collected in the form of a current to charge device 100. An example chemical reaction is shown at 600 in FIG. 6 and may comprise three stages: initiation, propagation and termination. During initiation a voltage may be applied across a molecule to cause the formation of free alkyl radicals. Propagation then arises through the formation of free alkyl radicals and peroxy-radicals. Termination may result in the formation of non-radical products. An example reaction on oleic acid as illustrated at 600 may require 2.9 mass units of oxygen per unit of fatty acid. It should be noted that the example oxidation reaction shown at 600 is different from a normal metabolic process wherein specific enzymes and cell structures are required. Moreover, reaction 600 is also different from the partial oxidation of lipoproteins that may occur in an organic body, which mostly affects the protein shell rather than the lipid core of oleic molecules. In this reaction oxidized LDL precipitates on the walls of blood vessels, leading to detrimental health issues like atherosclerosis, cardiac problems, etc. In contrast, embodiments consistent with the present disclosure target the complete oxidation of LDL. So, as a result of the oxidation process "bad" LDL molecules may be destroyed to generate power for device 100, the other byproducts being $CO_2$ and $H_2O$ that are harmless to most organic bodies.

As shown at 602, a voltage 604 may be applied across LDL molecule 504 (e.g., through circuitry 500). Voltage 604 may combine with oxygen 606 present in the organic body (e.g., in the bloodstream of a human body) to initiate oxidation 608 in LDL molecule 504. In general, oxidation 606 may be a "burning" reaction in which oxygen feeds the reaction and may create excess electrons and heat as the products of the reaction. Lipoproteins like LDL molecule 504 are molecular complexes containing proteins on their surface and lipids (e.g., such as triacylglycerol and cholesterol) inside. These types of molecules store energy chemically, and are well-suited for use in generating electrical current via oxidation. As shown at 610, as LDL molecule 504 may break down (e.g., in parts 504A and 504B) while creating a current of excess electrons 612 and heat 614 as products of the reaction. Consistent with various embodiments of the present disclosure, electrons 610 and heat 612 may be employed to charge energy storage modules 112. In particular, electrons 610 may form a current (e.g., currents 312 and 314) for charging energy storage modules 112 directly, and thermoelectric generation module 110 may employ heat 612 for generating a second current for charging energy storage modules 112.

In an example of operation, a typical concentration of LDL in human blood is 2.6 to 3.3 mmol/l (e.g., 100 to 129 mg/dl), yielding a $\rho_{LDL}$ of approximately 1 kg/m$^3$. Oxygen ($O_2$) has partial pressure p=10-13 kPa that may translate to concentration n=p/kT=2.4e24/m$^3$ of oxygen molecules or density of $\rho_{O2}$=0.13 kg/m$^3$. Therefore, the oxidation reaction may be limited by the supply of oxygen by the factor of Chlim=0.13/2.9=0.044 for the case wherein oleic acid is being oxidized. The output of energy in oxidation of lipids is about Espe=9 kcal/g, where kcal=4200 J, or Espe=3.8e7 J/kg. Presuming that an amount of LDL flowing towards a chip of area=1 mm$^2$ with the speed of blood of v=0.1 m/s is Mflow=$\rho$LDL*A*v=10$^{-7}$ kg/s [@mm$^2$], the extractable power from this flow is Pflow=Mflow*Espe*Chlim=160 mW [@mm$^2$]. Taking an example chip area of the chip of 0.1 mm$^2$, the extractable power of the chip, 16 mW, exceeds the predicted electrical requirement of device 100. Of course, the above calculation assumes 100% efficiency, and in actual practice not all chemical energy may be converted to electrical power.

Also, some energy is required to trigger the reaction. For example reactions, it is of the order of 10 Kcal/mole for oleic acid, wherein Etri is approximately 1.5e5 J/kg. Given a supply voltage of V=0.2V, LDL resistance is approximately the resistance of one channel of quantum conduction through a molecule Rq=25 kOhm, and given a pulse duration of 1 ns, the Joule heat dissipated from the pulse eJ=V$^2$*tau/Rq, which is approximately 1.6 fJ. Most importantly, the amount of energy needed to trigger the reaction is much smaller than the energy output. Per molecule of LDL having a diameter of 25 nm and a mass of m_LDL~1e-20 kg, the trigger energy would be approximately 1 fJ and the output energy would be approximately 400 fJ.

Alternatively, it may be possible to utilize a reduction-oxidation (redox) reaction instead of an oxidation reaction. The Redox reaction is in essence the same chemical reaction as above, but happening as two separate branches on the anode $C_{18}H_{34}O_2$+34 $H_2O$→18 $CO_2$+102 $H^+$+102 $e^-$, and on the cathode 102 $H^+$+102 $e^-$+25.5 $O_2$→51 $H_2O$. It is estimated that the ideal value of the current produced by the reaction via the number of electrons per molecule, $N_{elec}$=102 in this case, and the mass of the molecule is Mmolec=282*mproton, Iflow=Mflow*Chlim*Nelec/Mmolec*eelec=0.15 mA [@mm$^2$]. This corresponds to a voltage of approximately 1V. Real world current and voltage may be smaller due to imperfect conversion of chemical energy to electrical one.

In example heat-based generation, power may be generated by a thermoelectric junction. For example, the junction may be composed of n- and p-doped wires of a material with a high figure of merit ZT such as, but not limited to, PbTe, $Bi_2Te_3$ or $Bi_2Se_3$ nanostructures, silicon nanowires, etc. The thermoelectric junction may be deposited next to molecular sieve 108 and connected by the power carrying conductor (e.g. of copper wires). During oxidation, heat may be emitted that raises the temperature of molecular sieve 108. The maximum efficiency $\eta_{max}$ may then be determined by:

$$\eta_{max} = \frac{T_H - T_C}{T_H} \frac{\sqrt{1+Z\overline{T}} - 1}{\sqrt{1+Z\overline{T}} + \frac{T_C}{T_H}} \tag{1}$$

wherein $T_H$ is the temperature at the hot junction and $T_C$ is the temperature in equation (1). Using $Bi_2Te_3$ as an example, the high ZT=0.5. The temperature rise is then approximately:

$$T_H - T_C = P_{flow} * \frac{\text{length}^2}{\frac{\text{thickness}}{\sigma}} = 530 \text{ K} \tag{2}$$

Wherein, given $Bi_2Te_3$ as an example, thermal conductance of $\sigma$=1.20 W/(m·K), length=20 um, thickness=0.1 um and $\eta_{max}$=15%. Given $A_{sieve}$=0.1 mm$^2$, the electric power generated may be:

$$P_{elec} = P_{flow} * A_{sieve} * \eta_{max} = 2.4 \text{ mW} \tag{3}$$

Figure 7:
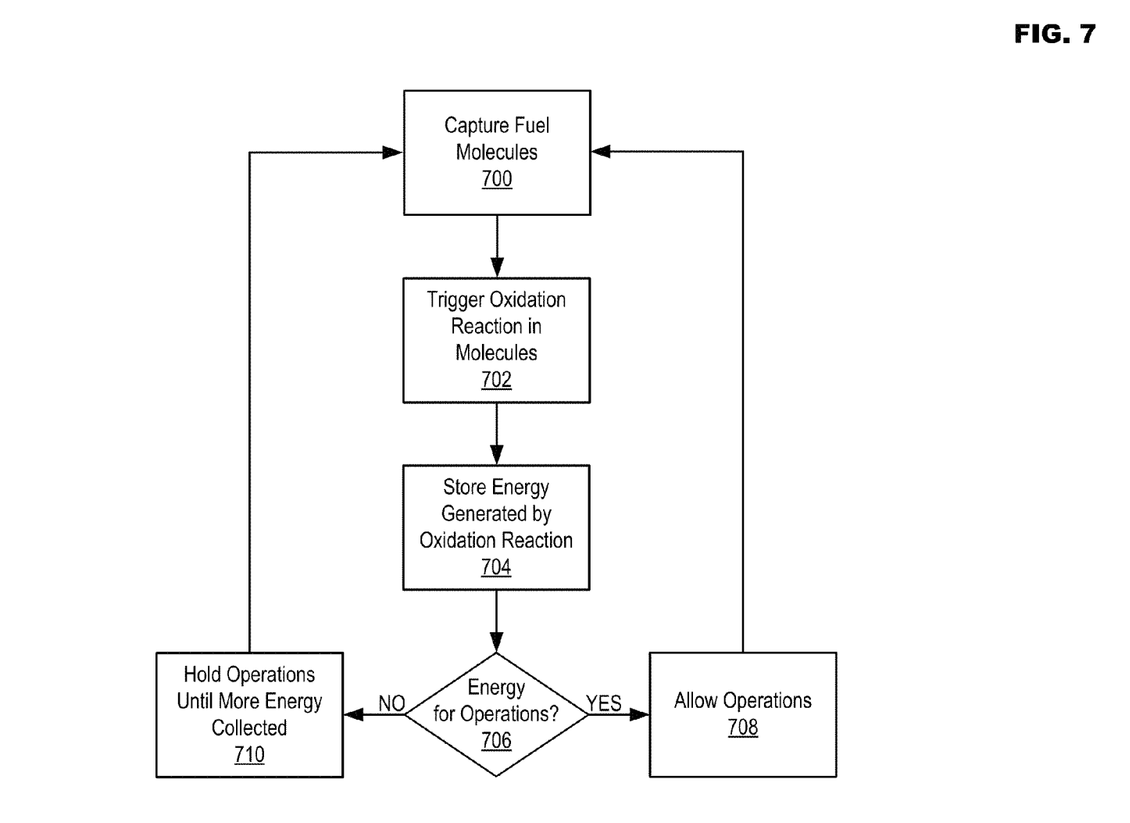
FIG. 7 illustrates example operations for a self-powered internal medical device in accordance with at least one embodiment of the present disclosure.

FIG. 7 illustrates example operations for a self-powered internal medical device in accordance with at least one embodiment of the present disclosure. In operation 700, a device may capture molecules (e.g., LDL molecules) in which an oxidation reaction may be initiated, the oxidation reaction being used to generate energy for operating the device. The oxidation reaction may then be initiated in operation 702, and energy generated by the oxidation reaction may be stored in operation 704. For example, the oxidation reaction may generate current and heat. The generated current may be employed to directly charge energy storage modules in the device, while the heat may be employed by a thermoelectric generation module in the device to generate a secondary current for charging the energy storage modules. A determination may then be made in operation 706 as to whether there is enough energy in the device for operations not related to power generation (e.g., body characteristic sensing and/or communication-related operations). If in operation 706 it is determined that there is enough energy for the non-energy-related operations (e.g., if the amount of energy in the device is above a certain threshold), then in operation 708 these operation may be allowed. Otherwise, if in operation 706 it is determined that there is not enough energy to sustain non-energy-related operations then in operation 710 the non-energy-related operations may be held until more energy is collected. Operations 708 and 710 may be followed by a return to operation 700 to continue energy generation in the device.

While FIG. 7 illustrates operations according to an embodiment, it is to be understood that not all of the operations depicted in FIG. 7 are necessary for other embodiments. Indeed, it is fully contemplated herein that in other embodiments of the present disclosure, the operations depicted in FIG. 7, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

As used in this application and in the claims, a list of items joined by the term "and/or" can mean any combination of the listed items. For example, the phrase "A, B and/or C" can mean A; B; C; A and B; A and C; B and C; or A, B and C. As used in this application and in the claims, a list of items joined by the term "at least one of" can mean any combination of the listed terms. For example, the phrases "at least one of A, B or C" can mean A; B; C; A and B; A and C; B and C; or A, B and C.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage mediums. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smartphones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry. Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), embedded multimedia cards (eMMCs), secure digital input/output (SDIO) cards, magnetic or optical cards, or any type of media suitable for storing electronic instructions. Other embodiments may be implemented as software modules executed by a programmable control device.

Thus, this disclosure is directed to a self-powered internal medical device. An example device may comprise at least an energy generation module and an operations module to at least control the energy generation module. The energy generation module may include a structure to capture certain molecules in the organic body based at least on size, the structure including a surface of the device in which at least one opening is formed. The at least one opening may be sized to only capture certain molecules. The operations module may initiate oxidation reactions in the captured molecules to generate current for device operation or for storage in an energy storage module. Thermoelectric generation circuitry in the energy generation module may also use heat from the reaction to generate a second current. The operations module may control operation of a sensor module and/or communication module in the device based on the generated energy.

The following examples pertain to further embodiments. The following examples of the present disclosure may comprise subject material such as a device, a method, at least one machine-readable medium for storing instructions that when executed cause a machine to perform acts based on the method, means for performing acts based on the method and/or a system pertaining to a self-powered internal medical device, as provided below.

Example 1

According to this example there is provided a device including an energy generation module to generate energy based on molecules captured from an organic body in which the device is implanted, the molecules being captured based at least on size and an operations module to at least control operation of the energy generation module.

Example 2

This example includes the elements of example 1, wherein the device is sized to be implantable within a blood vessel of the organic body.

Example 3

This example includes the elements of any of examples 1 to 2, wherein the energy generation module is to cause a chemical reaction to occur in the captured molecules to at least generate electrical current.

Example 4

This example includes the elements of any of examples 1 to 3, wherein the energy generation module comprises at least one surface of the device in which is formed at least one opening, the at least one opening being sized to capture molecules of a first size and to allow molecules of a second size to escape capture.

Example 5

This example includes the elements of example 4, wherein a plurality of openings are formed in the at least one surface to form a molecular sieve for capturing a plurality of molecules of the first size.

Example 6

This example includes the elements of any of examples 4 to 5, wherein the at least one surface is formed on the device using silicon underetch with electrodes on the at least one surface and an opposing surface of the device, the electrodes being at least structurally coupled by a silicon via formed through the device.

Example 7

This example includes the elements of any of examples 4 to 6, wherein beneath the at least one surface of the device are material layers comprising at least one of Nafion or a mesh of carbon nanotubes.

Example 8

This example includes the elements of any of examples 4 to 7, wherein the molecules of a first size are low-density lipoprotein (LDL) molecules and the molecules of a second size are high-density lipoprotein (HDL) molecules.

Example 9

This example includes the elements of example 8, wherein the operations module is to initiate an oxidation reaction in the captured LDL molecules by causing a voltage to be placed across the captured LDL molecules, the oxidation reaction causing a first electrical current and heat to be generated.

Example 10

This example includes the elements of example 9, wherein the energy generation module comprises thermoelectric generation circuitry to generate a second electrical current based on the generated heat.

Example 11

This example includes the elements of example 10, wherein the thermoelectric generation circuitry comprises at least sections of the device upon which are deposited N-doped and P-doped Bismuth Telluride.

Example 12

This example includes the elements of any of examples 10 to 11, wherein at least one of the first electrical current or the second electrical current is stored by at least one energy storage module also in the device.

Example 13

This example includes the elements of any of examples 1 to 12, wherein the operations module comprises at least a control module, a communication module and a sensor module.

Example 14

This example includes the elements of example 13, wherein the control module is to control the operation of the energy generation module by periodically supplying a voltage to the energy generation module.

Example 15

This example includes the elements of any of examples 13 to 14, wherein the sensor module is to sense at least one characteristic of the organic body and the communication module is to transmit information about at least one of the device or the at least one characteristic via wireless communication.

Example 16

This example includes the elements of example 15, wherein the information about the device comprises at least one of device identification, device operational status or device position.

Example 17

This example includes the elements of any of examples 15 to 16, wherein the information about the at least one characteristic of the organic body comprises blood component levels including at least one of oxygenation, glucose, red cell counts, white cell counts, salt concentration, metabolism byproducts or conditional precursors.

Example 18

This example includes the elements of any of examples 15 to 17, wherein the information about the at least one characteristic of the organic body comprises at least one of neuron electrical characteristics, concentration of neurotransmitters in synapses, stress from muscle contractions, exposure to sun, radiation or chemicals.

Example 19

This example includes the elements of any of examples 13 to 18, wherein the control module is further to control operation of at least one of the sensor module and the communication module based on the energy in the device.

Example 20

This example includes the elements of example 19, wherein the control module is further to determine the amount of energy in the device and to permit operation of the sensor module and the communication module when it is determined enough energy exists in the device to support the operation.

Example 21

This example includes the elements of any of examples 1 to 20, wherein the operations module comprises at least a control module to control the operation of the energy generation module by periodically supplying a voltage to the energy generation module, a sensor module to sense at least one characteristic of the organic body and a communication module is to transmit information about at least one of the device or the at least one characteristic via wireless communication.

Example 22

According to this example there is provided a method including capturing molecules from an organic body in which a device is implanted, the molecules being captured based at least on size, triggering energy generation in the device, the energy being generated based on the captured molecules and controlling operations in the device based on the energy generation.

Example 23

This example includes the elements of example 22, and further comprises causing a reaction to occur in the captured molecules to at least generate a first current and charging an energy storage module in the device based on the first current.

Example 24

This example includes the elements of example 23, wherein capturing molecules comprises capturing low-density lipoprotein (LDL) molecules and triggering energy generation comprises triggering an oxidation reaction in the captured LDL molecules.

Example 25

This example includes the elements of example 24, wherein causing a reaction to occur comprises causing a voltage to be placed across the captured LDL molecules, the oxidation reaction causing a first electrical current and heat to be generated.

Example 26

This example includes the elements of example 25, and further comprises generating a second current based on the heat generated by the reaction using thermoelectric generation circuitry in the device and charging the energy storage module in the device based on the second current.

Example 27

This example includes the elements of any of examples 22 to 26, wherein controlling operations comprises determining if there is enough energy in the device to allow at least one of a sensor module or communication module in the device to operate.

Example 28

This example includes the elements of example 27, and further comprises, if it is determined that there is enough energy in the device, causing the sensor module to sense at least one characteristic of the organic body and causing the communication module to transmit information about at least one of the device or the at least one characteristic via wireless communication.

Example 29

This example includes the elements of any of examples 22 to 28, wherein controlling operations comprises determining if there is enough energy in the device to allow at least one of a sensor module or communication module in the device to operate, if it is determined that there is enough energy in the device, causing the sensor module to sense at least one characteristic of the organic body and causing the communication module to transmit information about at least one of the device or the at least one characteristic via wireless communication.

Example 30

According to this example there is provided a system comprising at least a device, the system being arranged to perform the method of any of the examples 22 to 29.

Example 31

According to this example there is provided a chip set arranged to perform the method of any of the examples 22 to 29.

Example 32

According to this example there is provided at least one machine readable medium comprising a plurality of instructions that, in response to be being executed on a computing device, cause the computing device to carry out the method according to any of the examples 22 to 29.

Example 33

According to this example there is provided a self-powered internal medical device arranged to perform the method of any of the examples 22 to 29.

Example 34

According to this example there is provided a device having means to perform the method of any of the examples 22 to 29.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed:

1. A bioimplantable device, comprising:
an energy generation module to generate energy based on captured molecules, wherein the captured molecules are captured from an organic body in which the device is implanted and are captured by the energy generation module based at least at least in part on their size; and
an operations module to at least control operation of the energy generation module, the operations module comprising a control module, wherein the control module comprises circuitry configured to initiate oxidation of said captured molecules at least in part by supplying a voltage to said energy generation module.

2. The device of claim 1, wherein the energy generation module is configured to initiate oxidation of said captured molecules in response to said voltage from said control module, so as to produce electrical current.

3. The device of claim 1, wherein the energy generation module comprises at least one surface comprising at least one opening, wherein the at least one opening is sized to capture molecules of a first size and to allow molecules of a second size to escape capture.

4. The device of claim 3, further comprising electrodes are formed on the at least one surface and an opposing surface of the device, the electrodes being at least structurally coupled by a silicon via formed through the device.

5. The device of claim 3, wherein
the captured molecules are said molecules of a first size;
said molecules of a first size are low-density lipoprotein (LDL) molecules; and
the molecules of a second size are high-density lipoprotein (HDL) molecules.

6. The device of claim 5, wherein the control module is configured to initiate said oxidation by causing a voltage to be placed across the captured molecules, thereby generating a first electrical current and heat.

7. The device of claim 6, wherein the energy generation module comprises thermoelectric generation circuitry to capture at least a portion of said heat and to generate a second electrical current therefrom.

8. The device of claim 7, further comprising an energy storage module configured to store at least one of the first electrical current or the second electrical current.

9. The device of claim 1, wherein the operations module further comprises a communication module and a sensor module.

10. The device of claim 1, further comprising an energy storage module configured to store energy produced by the energy generation module, wherein the circuitry of the control module is to control the oxidation of said captured molecules in response to expiration of at least one of a time or a threshold level of energy stored in said energy storage module.

11. The device of claim 9, wherein the sensor module is to sense at least one characteristic of the organic body and the communication module is to transmit information about at least one of the device or the at least one characteristic via wireless communication.

12. The device of claim 1, wherein the circuitry of the control module is further to control oxidation of the captured molecules at least in part in response to sensing a presence of at least one of said captured molecules.

13. A method, comprising:
with an energy generation module of a bioimplantable device, capturing molecules from an organic body in which the device is implanted based at least in part on their size;
with control circuitry of an operations module of said device, initiating oxidation of said captured molecules at least in part by supplying a voltage to said energy generation module, said oxidation to produce at least one electrical current.

14. The method of claim 13, wherein said at least one electrical current comprises a first electrical current, and the method further comprises:
charging an energy storage module in the device at least in part with the first electrical current.

15. The method of claim 14, wherein said captured molecules comprise low-density lipoprotein (LDL) molecules, and said oxidation results in the complete oxidation of said LDL molecules.

16. The method of claim 14, wherein:
said oxidation produces heat;
said energy generation module further comprises thermoelectric generation circuitry; and
the method further comprises converting at least a portion of said heat with said thermoelectric generation circuitry into a second electrical current; and
charging the energy storage module in the device based on the second current.

17. The method of claim 13, wherein said device further comprises an energy storage module, a sensor module, and a communication module, and the method further comprises:
determining, with said control circuitry, whether there is a threshold amount of energy in the energy storage module, the threshold amount of energy being sufficient to enable at least one of the sensor module or the communication module to operate; and
controlling, with said control circuitry, causing at least one of said sensor module or said communication module to operate when it is determined that an amount of energy in said energy storage module exceeds said threshold amount.

18. The method of claim 17, wherein:
causing said sensor module to operate comprises causing the sensor module to sense at least one characteristic of the organic body; and
causing said communication module to operate comprises causing the communication module to transmit information about at least one of the device or the at least one characteristic via wireless communication.

19. At least one non-transitory machine-readable storage medium having stored thereon, individually or in combination, instructions that when executed by one or more processors of a bioimplantable device result in the following operations comprising:
with an energy generation module of the device, capturing molecules from an organic body in which the device is implanted based at least in part on their size;
with control circuitry of an operations module of said device, initiating oxidation of said captured molecules at least in part by supplying a voltage to said energy generation module, said oxidation to produce at least one electrical current.

20. The non-transitory medium of claim 19, wherein said at least one electrical current comprises a first electrical current, and said medium further comprises instructions that when executed by said one or more processors result in the following operations comprising:
charging an energy storage module in the device at least in part with the first electrical current.

21. The non-transitory medium of claim 20, wherein said captured molecules comprise low-density lipoprotein (LDL) molecules, and said oxidation results in the complete oxidation of said LDL molecules.

22. The non-transitory medium of claim 20, wherein:
said oxidation produces heat;
said device further comprises thermoelectric generation circuitry; and
the non-transitory medium further comprises instructions that when executed by said one or more processors result in the following operations comprising:
converting at least a portion of said heat with said thermoelectric generation circuitry into a second electrical current; and
charging the energy storage module in the device based on the second current.

23. The non-transitory medium of claim 19, wherein said device further comprises an energy storage module, a sensor module, and a communication module, and said medium further comprises instructions wherein when executed by said one or more processors results in performance of the following operations comprising:
determining, with said control circuitry, whether there is a threshold amount of energy in the energy storage module, the threshold amount of energy being sufficient to enable at least one of the sensor module or the communication module to operate; and
controlling, with said control circuitry, causing at least one of said sensor module or said communication module to operate when it is determined that an amount of energy in said energy storage module exceeds said threshold amount.

24. The non-transitory medium of claim 23, further comprising instructions that when executed by one or more processors result in the following operations comprising:
causing said sensor module to operate comprises causing the sensor module to sense at least one characteristic of the organic body; and
causing said communication module to operate comprises causing the communication module to transmit information about at least one of the device or the at least one characteristic via wireless communication.

* * * * *